United States Patent
Norén et al.

(10) Patent No.: US 7,215,996 B2
(45) Date of Patent: May 8, 2007

(54) BI-VENTRICULAR HEART STIMULATING DEVICE, SYSTEM AND METHOD

(75) Inventors: Kjell Norén, Solna (SE); Karin Ljungström, Hässelby (SE); Sven Kalling, Täby (SE); Lars Mandal, Solna (SE); Anders Björling, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 232 days.

(21) Appl. No.: 10/499,253

(22) PCT Filed: Oct. 4, 2002
(Under 37 CFR 1.47)

(86) PCT No.: PCT/SE02/01817

§ 371 (c)(1),
(2), (4) Date: Jun. 17, 2004

(87) PCT Pub. No.: WO03/051457

PCT Pub. Date: Jun. 26, 2003

(65) Prior Publication Data
US 2005/0125042 A1 Jun. 9, 2005

(30) Foreign Application Priority Data
Dec. 19, 2001 (SE) ..................... 0104337

(51) Int. Cl.
*A61N 1/365* (2006.01)
(52) U.S. Cl. .............. 607/17; 607/9; 607/18; 607/25

(58) Field of Classification Search ............ 607/9, 607/17–18, 25
See application file for complete search history.

(56) References Cited

U.S. PATENT DOCUMENTS

| 4,686,987 | A | 8/1987 | Salo et al. |
|---|---|---|---|
| 5,154,171 | A | 10/1992 | Chirife |
| 5,720,768 | A | 2/1998 | Verboven-Nelissen |
| 6,070,100 | A | 5/2000 | Bakels et al. |
| 2001/0012953 | A1 | 8/2001 | Molin |
| 2001/0021864 | A1 | 9/2001 | Molin |
| 2001/0034540 | A1 | 10/2001 | Molin |
| 2001/0049543 | A1 | 12/2001 | Kroll |

FOREIGN PATENT DOCUMENTS

EP 0 532 148 3/1993

*Primary Examiner*—Robert E. Pezzuto
*Assistant Examiner*—Shevon Johnson
(74) *Attorney, Agent, or Firm*—Schiff Hardin LLP

(57) ABSTRACT

In an implantable heart stimulating device, system and method, electrical stimulation pulses are delivered to first and second ventricles of a heart with a variable time interval therebetween, and signals are sensed at two different positions in the heart, from which an impedance value is derived. A minimum value and a maximum value of the impedance value are determined during a heart cycle, and a relationship between the minimum and maximum values also is determined. The time interval is varied and the relationship is monitored over a number of heart cycles. The time interval is set so that the relationship satisfies a predetermined requirement.

16 Claims, 4 Drawing Sheets

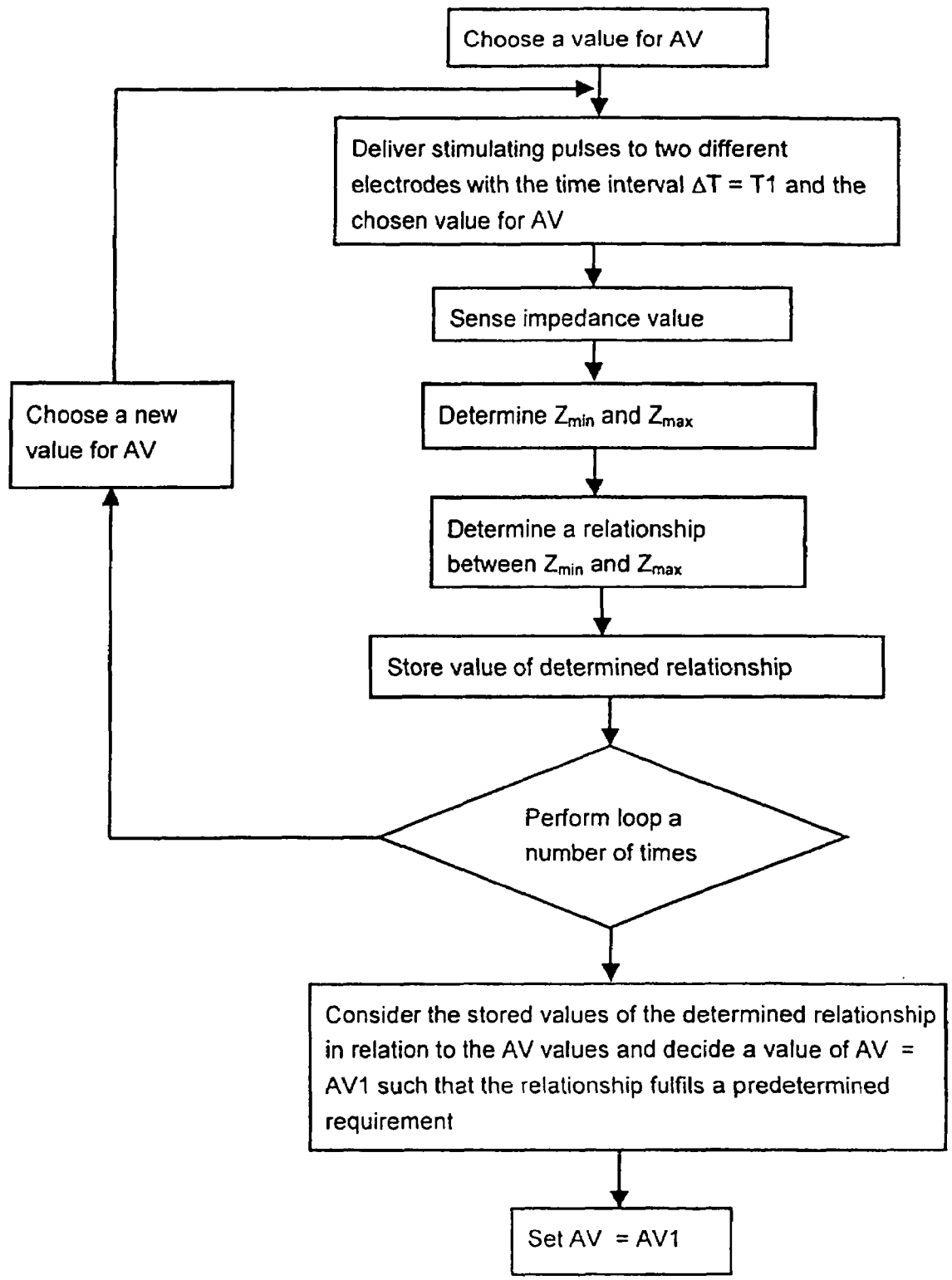

BI-VENTRICULAR HEART STIMULATING DEVICE, SYSTEM AND METHOD

BACKGROUND OF THE INVENTION

1. Field of the Invention

The present invention relates to an implantable heart stimulating device, a system including such a device and a method for heart stimulation using the system. More precisely, the invention concerns a stimulating device of the type having a housing and a control circuit arranged in the housing. The heart stimulating device is designed such that it can be used to stimulate both ventricles of a heart.

2. Description of the Prior Art

Most heart stimulating devices, or pacers, are designed to stimulate the right ventricle of the heart. It is also known to stimulate the left ventricle. In particular for the treatment of congestive heart failure (CHF) or other severe cardiac failures, it is known to stimulate the left ventricle, or both ventricles, in order to optimize the hemodynamic performance of the heart.

U.S. Pat. No. 5,720,768 describes different possible electrode positions in order to stimulate or sense the different chambers of the heart.

In different kinds of heart stimulating devices it is also known to use an impedance value in order to control different pacing parameters.

U.S. Pat. No. 5,154,171 describes the use of impedance values to control the pacing rate. The pacer described in this document is designed only to stimulate the right side of the heart.

U.S. Pat. No. 6,070,100 describes that electrodes may be positioned in both the left atrium and the right atrium as well in the left and the right ventricles. The patent describes the possibility of sensing the impedance between different electrodes. The sensed impedance values may be used to improve the cardiac output.

United States Patent Publication No. 2001/0012953 describes bi-ventricular pacing. An impedance may be measured between electrodes on the right and the left sides of the heart. The variation of the impedance with time is detected. The detected impedance variation may be used in order to synchronize the contraction of the ventricles.

United States Patent Publication No. describes different manners of using the proximal and distal electrodes of different leads in order to inject a current and to measure an impedance. The measured impedance value may be used in order to maximize the cardiac flow.

For a patient suffering from congestive heart failure (CHF) it is of a great benefit to be able to increase the cardiac output, thereby decreasing the degree of CHF. One cause of CHF is that the left and right ventricles are not synchronized with each other. By optimising the synchronization between the ventricles, the filling of the ventricles and the cardiac output may be increased.

SUMMARY OF THE INVENTION

An object of the present invention is to provide an implantable heart stimulating device which is able to deliver stimulating pulses to both the ventricles of a heart and which is able to control the delivery of the stimulating pulses such that the cardiac output is improved. A further object is to provide such a device which uses an impedance measurement in order to control the delivery of the stimulating pulses. A further object is to provide such a device which is able to improve the heart condition for a patient suffering from CHF. A still further object is to provide such a device which automatically finds an optimal time interval between stimulating pulses to the two ventricles. Another object is to provide such a device which in a relatively simple manner is able to automatically deliver the stimulating pulses in an optimal way. According to the invention, also a system including such a device and a method for stimulating about using the system are provided.

The above objects are achieved by an implantable heart stimulating device having a housing a control circuit in the housing, the control circuit being adapted to be connected to a first electrode to be positioned to stimulate a first ventricle of the heart, and the control circuit also being adapted to be connected to at least a second electrode to be positioned to stimulate the second ventricle of the heart. The control circuit controls delivery of electrical stimulating pulses to the first and second electrodes in order to stimulate the first and second ventricles, respectively, with the delivery of the stimulating pulses to the first and second electrodes occurring within the same cycle of the heart such that there is a time interval between them, with the time interval being variable. Sensing circuitry senses signals received from electrodes positionable at two different positions in the heart. The control circuit derives an impedance value based on the sensed signals, the impedance value being indicative of the impedance between the electrodes positionable at two different positions in the heart. The control circuit determines a minimum value and a maximum value of the impedance value during a heart cycle, and determines a relationship between the minimum and maximum values. The control circuit varies the time interval and monitors the relationship over a number of heart cycles, and sets the time interval such that the relationship satisfies a predetermined requirement.

It should be noted that the time interval may be chosen to be equal to zero, i.e. in this case stimulation signals are delivered simultaneously to the first and second electrodes. Furthermore, it should be noted that the time interval may be positive or negative, i.e. the first electrode may emit stimulating pulses before or after the second electrode. In a practical use of the device, the sensed signals may be derived from electrodes positioned on different sides of the left ventricle. By monitoring the impedance value between such electrodes, an indication of the volume of blood in the left ventricle may be obtained. The minimum and maximum values depend on the maximum and minimum, respectively, of the amount of blood in the ventricle. By determining the relationship and by setting the time interval such that the relationship satisfies a predetermined requirement, the delivery of the stimulating pulses to the first and second electrodes can be optimized in order to improve the cardiac output. In this manner, for example, the heart condition of a patient suffering from CHF may be improved.

In a preferred embodiment of the invention, the control circuit determines the ratio between the minimum value and said maximum value as the aforementioned relationship. If the electrodes between which the impedance value is derived are suitably positioned, the ratio is closely linked to the so-called ejection fraction (EF). It has been found to be advantageous to use this ratio for controlling the delivery of the stimulating pulses.

In another embodiment of the invention, the control circuit determines the difference between the minimum value and said maximum value. Also this difference can function as an indication of the cardiac output and may therefore also be advantageously used for controlling the delivery of the stimulating pulses.

In a further embodiment of the invention, the control circuit determines the ratio between the minimum value and the difference between said minimum value and the maximum value as the aforementioned relationship. This particular ratio is even closer linked to the EF if the electrodes between which the impedance value is derived are suitably positioned in relation to the heart. It should be noted that preferably this ratio refers to the absolute value of the division between the minimum value and difference, since if the difference is negative the ratio would otherwise be negative. It is therefore preferably the magnitude of the ratio employed.

In a further embodiment of the invention, the predetermined requirement is that the ratio is minimized. By minimizing the ratio it has been found that an optimal cardiac output can be achieved. It should be noted that minimizing the ratio is of course the same as maximising the inverse of the ratio. This possibility is thus included in the definition of minimizing the ratio as used herein.

In a further embodiment of the invention, the control circuit operates such that the time interval is changed in a first direction, the first direction being either an increase or a decrease of the time interval and the control circuit monitors the change of the ratio when said time interval is changed in said first direction. If the ratio decreases, the time interval is further changed in the first direction until the predetermined requirement has been satisfied. This has been found to be an advantageous embodiment for finding the time interval at which the predetermined requirement is satisfied. For example, in this manner the minimum of the aforementioned ratio may be established.

In a further embodiment of the invention, the control circuit operates such that if the ratio increases, the time interval is changed in the opposite direction to the first direction, whereafter the interval is further changed in said opposite direction until the predetermined requirement has been established. In this embodiment, it is established that the time interval is changed in the correct direction such that the predetermined requirement may be satisfied in an efficient manner.

In another embodiment of the invention, the control circuit operates to enable the reception of signals indicating the activity level of a living being into which the heart stimulating device is implanted, and the control circuit is arranged such that the varying and setting of the time interval are performed at a time when the signals indicate a low level of activity. Preferably, the optimal time interval thus is established while the patient in question is at rest. This is made possible by this embodiment, according to which the control circuit is also able to detect the level of activity of the living being in question.

In a further embodiment of the invention, the control circuit operates to enable the delivery of stimulating pulses in which at least one atrio-ventricular delay is controllable, and the control circuit keeps the time interval at the set value, and to: varies the atrio-ventricular delay and monitors the relationship over a number of heart cycles, and sets the atrio-ventricular delay such that the relationship satisfies the predetermined requirement. With the device operating in this manner, the output of a heart can be further improved.

In another embodiment of the invention, the control circuit is arranged to be connected to a first lead carrying the first electrode and a second lead carrying the second electrode. The sensing circuitry operates such that the sensed signals, receivable from electrodes positioned at two different positions, are received via these first and second leads, respectively. The heart stimulating device thus may be provided with a connector portion via which the control circuit may be connected to two different leads. Such leads may be positioned at different positions in relation to the heart. It is thereby possible to derive the impedance value between selected positions.

The above objects of the invention also are achieved by a heart stimulating system having a heart stimulating device according to any of the preceding embodiments and a first lead carrying at least the first electrode and a second lead carrying at least the second electrode, wherein said first and second leads are connected to the heart stimulating device such that said first and second electrodes are connected to the control circuit. The system thus includes the two leads connected to the heart stimulating device. With such a system the above advantages are achieved.

According to a preferred embodiment of the system, the system operates such that the impedance value is sensed between an electrode of the first lead and an electrode of the second lead. The leads may be positioned at suitable positions in relation to the heart. A suitable impedance value thus can be derived between electrodes of the first and second leads, respectively.

The objects of the invention also are achieved by a method for stimulating a heart using a heart stimulating system according to any of the above embodiments, wherein the first electrode is positioned to stimulate a first ventricle of a heart of a human or animal and the second electrode is positioned to stimulate the second ventricle of the heart. According to this method, the device is thus actually used to stimulate the two ventricles of a heart. In this method, the advantages described above in connection with the device are achieved.

According to a preferred manner of the method, the impedance value is sensed between two electrodes positioned such that the impedance value is measured across at least a part of one of said first and second ventricles. In this method of using the system, an indication of the amount of blood in the ventricle can be derived by the impedance value. The variation of this impedance value can be used as an indication of the amount of blood pumped by the ventricle.

In a preferred method of using the system, the ventricle, across which the impedance value is measured, is the left ventricle of the heart. To monitor the ejection fraction of the left ventricle is particularly important, for example when treating a patient suffering from CHF.

In a further method of using the system, an impedance value is sensed across at least a part of the left atrium of the heart. Also the variation in the amount of blood in the left atrium may be used to control the heart stimulating device.

DESCRIPTION OF THE DRAWINGS

FIG. 5 is a flow chart of the function of the heart stimulating device according to an embodiment of the invention for adjusting the AV-delay.

DESCRIPTION OF THE PREFERRED EMBODIMENTS

Figure 1:
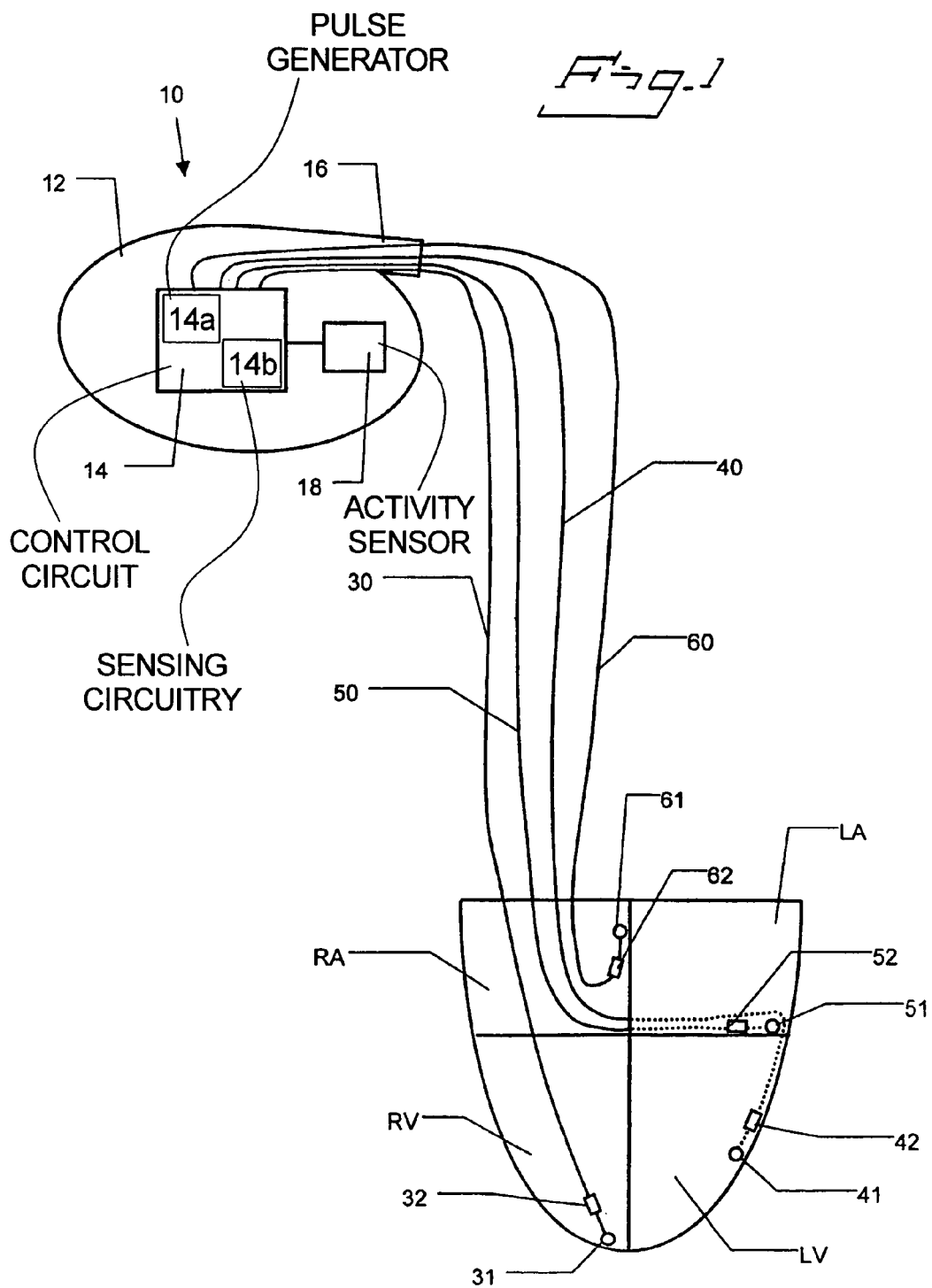
FIG. 1 schematically illustrates a heart stimulating device according to the invention connected to leads with electrodes positioned in a heart.

An embodiment of the invention will now first be described with reference to FIG. 1. FIG. 1 thus schematically shows an implantable heart stimulating device 10. The heart stimulating device 10 is hereinafter also called a pacer. Such a heart stimulating device 10 is well known to a person skilled in the art and will therefore not be described in all its details here. The pacer 10 has a housing 12. A control circuit 14 is arranged in the housing 12. The pacer 10 includes a connector portion 16 to which a number of leads 30, 40, 50, 60 may be attached.

A first lead 30 has a distal electrode 31 (also called tip electrode) and a proximal electrode 32 (also called ring electrode). In the shown embodiment the lead 30 is thus bipolar, however, it is also possible for one or more leads to be unipolar, i.e. it has only one electrode. The lead 30 includes electrical conductors (not shown) through which the electrodes 31, 32 are connected to the control circuit 14. The control circuit 14 is also adapted to be connected to a second lead 40, which has corresponding electrode surfaces 41, 42.

The pacer 10 also may be arranged such that it is connectable to further leads. FIG. 1 shows a third lead 50 with electrode surfaces 51, 52 and a fourth lead 60 with electrode surfaces 61, 62.

The control circuit 14 includes a pulse generator 14a emits stimulating pulses to different electrodes and sensing circuitry 14b that senses signals received from the electrodes. The details of the control circuit 14 to perform the emission of pulses and the sensing are known to those skilled in the art and therefore need not be shown in more detail here.

FIG. 1 also schematically shows a heart having a right atrium RA, a right ventricle RV, a left atrium LA and a left ventricle LV. In the illustrated embodiment the electrodes 31, 32 are positioned in a conventional manner near the apex of the right ventricle RV. The lead 40 is positioned such that the electrodes 41, 42 may be used for emitting stimulating pulses to the left ventricle LV. The lead 40 may for example be introduced through the right atrium RA, via the coronary sinus into the middle or great cardiac vein. In the shown embodiment a third lead 50 is introduced such that the electrodes 51, 52 are positioned in the coronary sinus, a fourth lead 60 is introduced such that the electrodes 61, 62 are positioned in the right atrium RA in a conventional manner.

The control circuit 14 operates such that it can deliver stimulating pulses to both ventricles RV, LV, for example to the electrodes 31 and 41. The control circuit 14 is thus operates such that stimulating pulses to the electrodes 31, 41 can be delivered within the same cycle of the heart (within the same heartbeat) with a time interval $\Delta T$ between the pulses to the electrodes 31 and 41. The control circuit 14 operates such that this time interval $\Delta T$ is variable. The time interval $\Delta T$ is sometimes also called the VV-interval. The control circuit 14 also operates such that it sense signals receivable from the different electrodes and such that an impedance value Z is derived based on sensed signals, the impedance value Z being indicative of the impedance between electrodes at two different positions of the heart. For example, the impedance may be measured between the electrodes 31, 32 of the first lead 30 and the electrodes 41, 42 of the second lead 40. The impedance value Z can be derived in different manners described in, for example, the above-cited documents. According to a preferred embodiment, a current is injected between electrodes 31 and 41 and the impedance value is measured between the ring electrodes 32, 42. It should be noted that it is also possible to derive an impedance value Z between other electrodes, for example between the electrodes 31, 32 of the first lead 30 and the electrodes 51, 52 of the third lead 50. Another possible impedance value is the impedance between the electrodes 51, 52 of the third lead 50 and the electrodes 61, 62 of the fourth lead 60.

The control circuit 14 operates such that it can determine a minimum value $Z_{min}$ and a maximum value $Z_{max}$ of the impedance during a heart cycle. Furthermore, the control circuit 14 determines a relationship between $Z_{min}$ and $Z_{max}$. The control circuit 14 varies the time interval $\Delta T$ and monitors the relationship over a number of heart cycles. Moreover, the control circuit 14 operates to set the time interval $\Delta T$ such that the relationship satisfies a predetermined requirement.

The pacer 10 also can be arranged to receive signals indicating the activity level of a living being into which the heart stimulating device 10 is implanted. Such signals, for example, can be produced by an activity sensor 18 included within the housing 12. Different kinds of activity sensors 18 are known to those skilled in the art. For example, such an activity sensor can sense the movement of the pacer 10 and thereby the movement of a being in which the pacer 10 is implanted. It is also possible to detect the activity of the patient by sensing signals received from different electrodes connected to the pacer 10.

Figure 3:
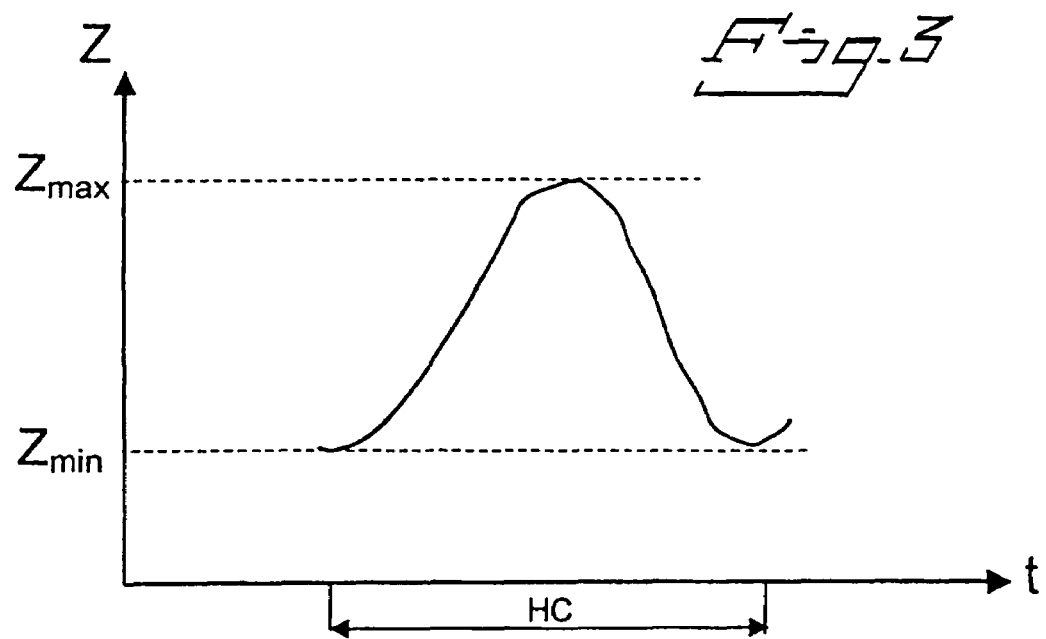
FIG. 3 schematically shows the variation of the impedance with time.

The impedance Z measured between, for example, the electrodes 32 and 42 depends on the amount of blood in the left ventricle LV. As the amount of blood in the ventricle LV varies during a heart cycle, the measured impedance value Z also varies. FIG. 3 illustrates schematically how the impedance value Z may vary with time t over a heart cycle HC. The impedance value Z is low when the ventricle LV is filled with blood. During the systolic phase, when the ventricle LV pumps out the blood, the impedance Z increases to a maximum value $Z_{max}$, whereafter the impedance value Z is lowered when the ventricle LV fills with blood during the diastolic phase. The control circuit 14 is thus determines $Z_{min}$ and $Z_{max}$ during a heart cycle may be determined. By sensing events in the heart, the control circuit 14 can distinguish different heart cycles from each other.

The difference $Z_{min}-Z_{max}$ is related to the stroke volume of the ventricle LV. The so-called ejection fraction EF is defined as the stroke volume divided by the end diastolic volume. The ejection fraction EF is thus related to $(Z_{min}-Z_{max})/Z_{min}$. Preferably, we may define the ejection fraction EF as the absolute value in order to always get a value that is larger than zero. The ejection fraction EF is also related to the value of $Z_{max}/Z_{min}$.

The control circuit 14 determines a relationship between $Z_{min}$ and $Z_{max}$. This relationship, for example, can be any of the above-described relationships which relate to the stroke volume or the ejection fraction EF. One example of this relationship is the ratio of $Z_{min}/Z_{max}$. The control circuit can be arranged to determine the time interval $\Delta T$ such that the ratio $Z_{min}/Z_{max}$ is minimized (or such that its inverse is maximized). The control circuit 14 is thus sets the time interval $\Delta T$ such that a predetermined requirement is satisfied. In this example, the predetermined requirement is thus that $Z_{min}/Z_{max}$ is minimized. By setting $\Delta T$ such that the predetermined requirement is satisfied, the stroke volume, or the ejection fraction EF, is controlled to be as large as possible. The cardiac output therefore is improved. To improve the cardiac output in this manner is important, for example, for a patient suffering from CHF.

Figure 2:
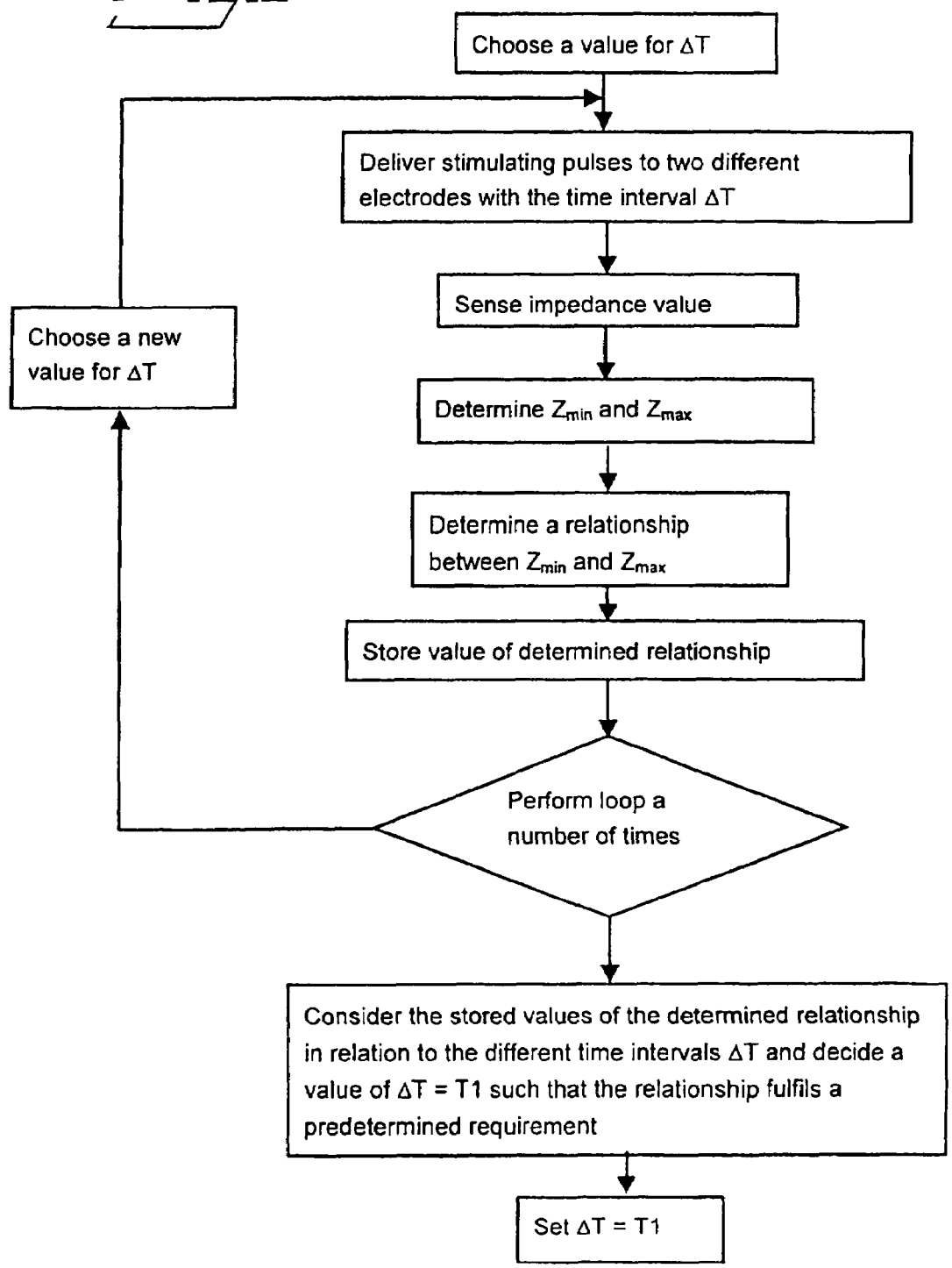
FIG. 2 is a flow chart of the function of the heart stimulating device according to one embodiment of the invention.

The flow chart of FIG. 2 illustrates how the control circuit 14 can operate. The flow chart starts by choosing a value for $\Delta T$. This value, for example, may be a previously set value for $\Delta T$ or that $\Delta T=0$. Stimulating pulses are thereafter delivered to the electrodes (for example to the electrodes 31 and 41) with the time interval $\Delta T$. The impedance value Z is sensed over at least a heart cycle. $Z_{min}$ and $Z_{max}$ are determined. In order to improve the measurement of $Z_{min}$ and $Z_{max}$ it is also possible to sense the impedance variation during several heart cycles before determining $Z_{min}$ and $Z_{max}$. $Z_{min}$ and $Z_{max}$ may in this case be the average value of $Z_{min}$ and $Z_{max}$, respectively, over several heart cycles.

Thereafter a relationship between $Z_{min}$ and $Z_{max}$ is determined. As pointed out above, this relationship may for example be $Z_{min}/Z_{max}$. The value of the determined relationship is stored. A new value for $\Delta T$ is set and the previous steps are carried out again in order to determine a new relationship between $Z_{min}$ and $Z_{max}$ and to store also this relationship. The new value for $\Delta T$ may be chosen in different manners. It is possible, for example, to change $\Delta T$ in a first direction, for example to increase $\Delta T$ with a small amount. The control circuit 14 then monitors whether the relationship $Z_{min}/Z_{max}$ increases or decreases. If this relationship decreases, the time interval $\Delta T$ may be further increased and the steps are carried out again in order to determine another relationship between $Z_{min}$ and $Z_{max}$. If ratio $Z_{min} Z_{max}$ were to increase, the time interval $\Delta T$ may be changed in the other direction, i.e. according to this example $\Delta T$ would then be decreased instead of increased. It should be noted that $\Delta T$ can even be negative if it is further decreased. Whether $\Delta T$ is positive or negative is thus decisive of which of the two ventricles is first stimulated. The loop illustrated in FIG. 2 is carried out a sufficient number of times such that it is possible to determine a $\Delta T$ for which the ratio $Z_{min}/Z_{max}$ is as low as possible.

Figure 4:
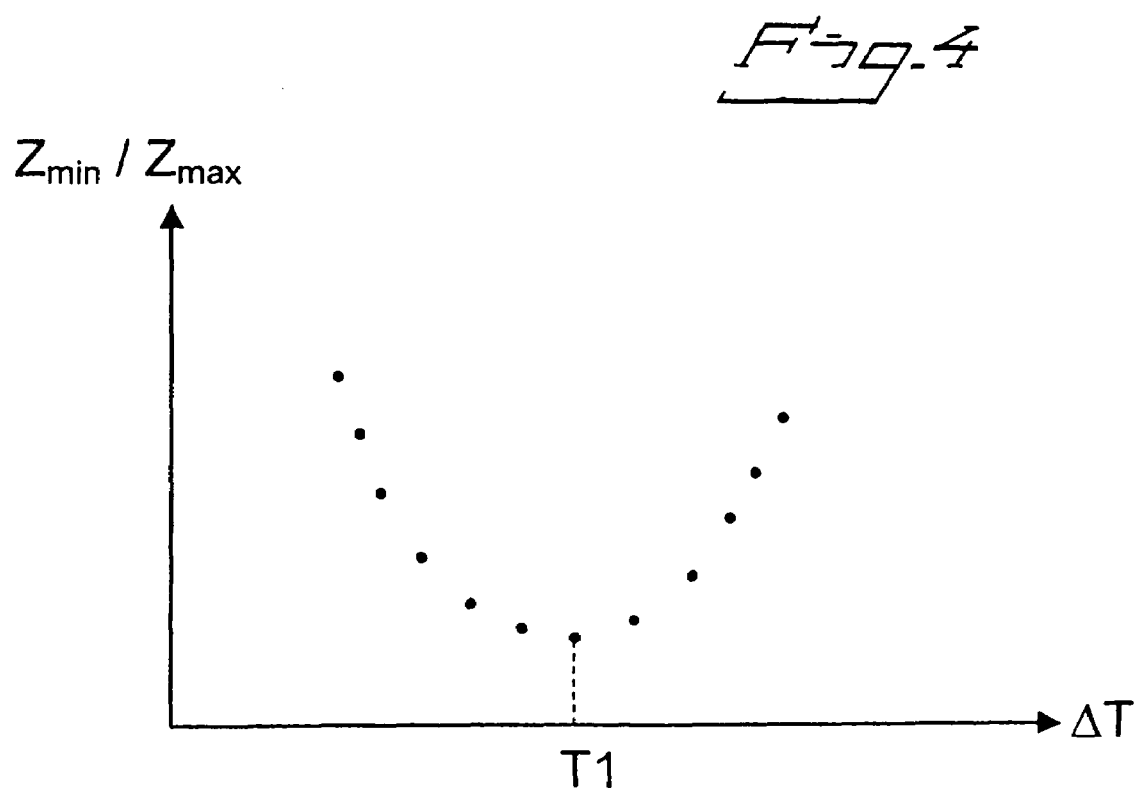
FIG. 4 schematically shows how a relationship between $Z_{min}$ and $Z_{max}$ depends on a time interval $\Delta T$.

In FIG. 4 the ratio $Z_{min}/Z_{max}$ as a function of $\Delta T$ is illustrated with a number of points. These points are thus obtained in the manner illustrated in FIG. 2 by determining the relationship $Z_{min}/Z_{max}$ for different values of $\Delta T$. The dots illustrated in FIG. 4 define a curve in which a minimum can be established. This minimum in FIG. 4 is obtained for $\Delta T=T1$. The control circuit 14 thus determines that at $\Delta T=T1$, the ratio $Z_{min}/Z_{max}$ satisfies the predetermined requirement, i.e. in this example that the ratio is as small as possible. When this has been decided, $\Delta T$ is set to be equal to T1. According to a preferred embodiment, the steps illustrated in FIG. 2 are carried out when the being into which the pacer 10 is implanted is at rest. This can be done, for example, at night when the person or animal in question is asleep. As stated above, the pacer 10 may detect the activity level. The control circuit 14 thus may operate such that the different steps are carried out when a signal indicates a low level of activity.

Once the time interval $\Delta T$ has been determined and set equal to T1, the control circuit 14 may carry out a similar determination in order to optimise a value for AV. AV is the so-called AV-delay. This is the time between an atrial sensed or paced event and the delivery of a ventricular output pulse. The AV-delay considered here may be, for example, the AV-delay for the right part of the heart. As is shown in FIG. 5, a certain value for AV is chosen. Thereafter stimulating pulses are delivered with this AV-delay and with the already set time interval $\Delta T=T1$. An impedance value Z is sensed. This impedance value Z can be the same impedance value as illustrated above. $Z_{min}$ and $Z_{max}$ are determined. A relationship between $Z_{min}$ and $Z_{max}$ is also determined, for example any of the above mentioned relationships. This relationship is stored. A new AV-delay is chosen. This can be done, for example, in an analogous manner to that according to which the new $\Delta T$ was chosen above. The previous steps are then carried out again and a new relationship is determined for the new AV-delay. The different stored relationships are considered together with the corresponding AV-values. A value AV=AV 1 is determined such that the predetermined requirement is satisfied, for example such that the ratio $Z_{min}/Z_{max}$ is as low as possible.

It is also possible to again perform the steps illustrated in FIG. 2 to possibly set a new $\Delta T$ if this is necessary in order to further improve the cardiac output.

In the embodiment discussed above, the impedance value was sensed between electrodes 31, 32 of the first lead and electrodes 41, 42 of the second lead. However, it is also possible to sense other impedance values in the heart as for example illustrated in the above-disclosed documents. For example, it is possible to sense an impedance value between electrodes 51, 52 of the third lead 50 and electrodes 61, 62 of the fourth lead 60. Such an impedance value may be an indication of the amount of blood in the left atrium LA. It is also possible to use this impedance value in order to control the time interval $\Delta T$ and the time interval AV in the same manner as illustrated above.

The heart stimulating device 10 according to the invention thus has a housing 12 with the control circuit 14 described above. However, the invention also relates to a heart stimulating system. This system includes the heart stimulating device 10 and at least a first lead 30 and a second lead 40 connected to the heart stimulating device 10 such that at least two electrodes 31, 41 are connected to the control circuit 14. The system is preferably operates such that the measured impedance value Z is sensed between an electrode 31 or 32 of the first lead 30 and an electrode 41 or 42 of the second lead 40.

The invention also relates to a method for stimulating a heart using such a heart stimulating system. According to this method, the first lead 30 is arranged such that the first electrode 31 and/or 32 is positioned to stimulate a first ventricle RV of a heart and the second lead 40 is arranged such that the second electrode 41 and/or 42 is positioned to stimulate the second ventricle LV of the heart. According to his method of using the device the above-illustrated steps are carried out.

The leads preferably are arranged such that the impedance value Z is measured across at least a part of one of said ventricles RV, LV, preferably across at least part of the left ventricle LV as has been discussed above. Alternatively or additionally, electrode 61, 62 and 51, 52 may be arranged such that an impedance value is sensed also across at least a part of the left atrium LA of the heart.

Although modifications and changes may be suggested by those skilled in the art, it is the invention of the inventors to embody within the patent warranted hereon all changes and modifications as reasonably and properly come within the scope of their contribution to the art.

The invention claimed is:

1. An implantable heart stimulating device comprising:
a housing adapted for implantation in a subject;
a pulse generator contained in said housing for interacting with a first ventricle and a second ventricle of a heart of the subject to stimulate said first ventricle and said second ventricle;

sensing circuitry contained in said housing adapted to obtain sensed signals from two different positions relative to the heart; and a control circuit contained in said housing and connected to said pulse generator and to said sensing circuitry, said control circuit controlling said pulse generator to emit respective stimulating pulses to the first and second ventricles within a same heart cycle with a time interval between the respective pulses that is variable by said control circuit, said control circuit receiving said sensed signals from said sensing circuitry and deriving an impedance value therefrom indicative of an impedance between said two different positions, said control circuit determining a minimum value magnitude and a maximum value magnitude of said impedance value during said heart cycle and determining a relationship between said minimum value magnitude and said maximum value magnitude, said control circuit varying said time interval and monitoring said relationship over a plurality of heart cycles, and said control circuit setting said time interval to cause said relationship to satisfy a predetermined requirement.

2. An implantable heart stimulating device as claimed in claim 1, wherein said control circuit forms a ratio of said minimum value magnitude and said maximum value magnitude as said relationship.

3. An implantable heart stimulating device as claimed in claim 2 wherein said predetermined requirement is that said ratio is minimized.

4. An implantable heart stimulating device as claimed in claim 1 wherein said control circuit forms a difference between said minimum value magnitude and said maximum value magnitude in determining said relationship.

5. An implantable heart stimulating device as claimed in claim 4 wherein said control circuit forms a ratio between said minimum value magnitude and said difference as said relationship.

6. An implantable heart stimulating device as claimed in claim 5 wherein said predetermined requirement is that said ratio is minimized.

7. An implantable heart stimulating device as claimed in claim 6 wherein said control circuit changes said time interval in a first direction selected from the group consisting of increasing said time interval and decreasing said time interval, and monitors a change in said ratio when said time interval is changed in said first direction and, if said ratio decreases, said control circuit further changing said time interval in said first direction until said predetermined requirement is satisfied.

8. An implantable heart stimulating device as claimed in claim 7 wherein said control circuit, if said ratio increases, changes said time interval in a direction opposite to said first direction, and further changes said time interval in said opposite direction until said predetermined requirement is satisfied.

9. An implantable heart stimulating device as claimed in claim 1 further comprising an activity sensor adapted to interact with the subject to obtain an activity signal indicative of a level of physical activity of the subject, and wherein said control circuit varies said time interval and monitors said relationship over a plurality of heart cycles and sets said time interval to cause said relationship to satisfy said predetermined requirement when said activity signal indicates said subject is at a low level of physical activity.

10. An implantable heart stimulating device as claimed in claim 1 wherein said pulse generator is also adapted to interact with an atrium of the heart to deliver stimulation pulses to the atrium, and wherein said control circuit controls delivery of respective stimulating pulses delivered to the atrium and to said ventricles with a variable atrial-ventricular delay, and wherein said control circuit, while maintaining said time interval at the set value, varies said atrial-ventricular delay and monitors said relationship over a plurality of heart cycles, and sets said atrial-ventricular delay to cause said relationship to satisfy said predetermined requirement.

11. An implantable heart stimulating system comprising:
a housing adapted for implantation in a subject;
a pulse generator contained in said housing for interacting with a first ventricle and a second ventricle of a heart of the subject to stimulate said first ventricle and said second ventricle;
sensing circuitry contained in said housing adapted to obtain sensed signals from two different positions relative to the heart; and
a control circuit contained in said housing and connected to said pulse generator and to said sensing circuitry, said control circuit controlling said pulse generator to emit respective stimulating pulses to the first and second ventricles within a same heart cycle with a time interval between the respective pulses that is variable by said control circuit, said control circuit receiving said sensed signals from said sensing circuitry and deriving an impedance value therefrom indicative of an impedance between said two different positions, said control circuit determining a minimum value magnitude and a maximum value magnitude of said impedance value during said heart cycle and determining a relationship between said minimum value magnitude and said maximum value magnitude, said control circuit varying said time interval and monitoring said relationship over a plurality of heart cycles, and said control circuit setting said time interval to cause said relationship to satisfy a predetermined requirement.

12. A heart stimulating system as claimed in claim 11 wherein said first lead carries said first sensing electrode and wherein said second lead carries said second sensing electrode.

13. A method for stimulating a heart comprising the steps of:
with a pulse generator contained in a housing implanted in a subject, stimulating a first ventricle and a second ventricle of a heart of the subject;
with sensing circuitry contained in said housing, obtaining sensed signals from two different positions relative to the heart; and
with a control circuit contained in said housing and connected to said pulse generator and to said sensing circuitry, controlling said pulse generator to emit respective stimulating pulses to the first and second ventricles within a same heart cycle with a time interval between the respective pulses that is variable by said control circuit, said control circuit receiving said sensed signals from said sensing circuitry and deriving an impedance value therefrom indicative of an impedance between said two different positions, determining a minimum value magnitude and a maximum value magnitude of said impedance value during said heart cycle and determining a relationship between said minimum value magnitude and said maximum value magnitude, and varying said time interval and monitoring said relationship over a plurality of heart cycles, and setting said time interval to cause said relationship to satisfy a predetermined requirement.

14. A method as claimed in claim 13 wherein the step of sensing said impedance between said two positions comprises sensing said impedance across at least a portion of one of said first ventricle and said second ventricle.

15. A method as claimed in claim 13 wherein the step of sensing said impedance between said two positions comprises sensing said impedance across a left ventricle of the heart.

16. A method as claimed in claim 13 wherein the step of sensing said impedance between said two positions comprises sensing said impedance across at least a part of a left atrium of the heart.

* * * * *